US012788507B2

(12) United States Patent
Hibner et al.

(10) Patent No.: US 12,788,507 B2
(45) Date of Patent: Nov. 10, 2026

(54) END OF LIFE INDICATOR FOR ROBOTIC SURGICAL INSTRUMENTS

(71) Applicant: Cilag GmbH International, Zug (CH)

(72) Inventors: John A. Hibner, Maineville, OH (US); Andrew O. Crews, Maineville, OH (US); Austin E. Wise, Cincinnati, OH (US); Emily M. Ross, Cincinnati, OH (US); Madison R. Taylor, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 191 days.

(21) Appl. No.: 18/772,857

(22) Filed: Jul. 15, 2024

(65) Prior Publication Data

US 2025/0025245 A1 Jan. 23, 2025

Related U.S. Application Data

(60) Provisional application No. 63/528,218, filed on Jul. 21, 2023.

(51) Int. Cl.
*A61B 34/30* (2016.01)
*A61B 17/00* (2006.01)
*A61B 90/00* (2016.01)

(52) U.S. Cl.
CPC ..... *A61B 34/30* (2016.02); *A61B 2017/00115* (2013.01); *A61B 2090/0807* (2016.02)

(58) Field of Classification Search
CPC .......... A61B 34/30; A61B 2017/00115; A61B 2090/0807
See application file for complete search history.

(56) References Cited

U.S. PATENT DOCUMENTS

| | | | |
|---|---|---|---|
| 2013/0150860 A1 | 6/2013 | Sidebotham et al. | |
| 2016/0361048 A1 | 12/2016 | Alden et al. | |
| 2020/0330120 A1* | 10/2020 | Koch, Jr. | A61B 17/320016 |
| 2022/0105638 A1* | 4/2022 | Zhang | B25J 13/06 |
| 2022/0105639 A1* | 4/2022 | Zhang | B25J 9/1689 |
| 2023/0115444 A1 | 4/2023 | Goodman et al. | |
| 2023/0181207 A1* | 6/2023 | Kingsley | A61B 34/30 606/167 |
| 2024/0325100 A1* | 10/2024 | Wise | A61B 34/70 |

OTHER PUBLICATIONS

International Search Report and Written Opinion, received for PCT Application No. PCT/IB2024/057013, mailed on Nov. 8, 2024, 27 pages.

* cited by examiner

*Primary Examiner* — Eyamindae C Jallow
(74) *Attorney, Agent, or Firm* — Joshua D. Young

(57) ABSTRACT

A surgical tool includes a drive housing, an indicator assembly arranged within the drive housing and actuatable to provide visual indication that the surgical tool has exhausted its useful life. The indicator assembly includes a drive input rotatably coupled to the bottom of the drive housing. The drive input further including a riser and a rim where the riser contains a passage therethrough. The indicator assembly further includes an indicator shaft extending through the passage along a longitudinal axis coaxially aligned with the drive input. The drive input is rotated to actuate the indicator assembly between a non-activated state, where the indicator shaft is recessed into the drive housing, and an activated state, where the indicator shaft extends out of the drive housing to provide the visual indication.

23 Claims, 10 Drawing Sheets

END OF LIFE INDICATOR FOR ROBOTIC SURGICAL INSTRUMENTS

PRIORITY

This application claims priority to U.S. Provisional Pat. App. No. 63/528,218, filed on Jul. 21, 2023.

BACKGROUND

Minimally invasive surgical (MIS) instruments are often preferred over traditional open surgical devices due to reduced post-operative recovery time and minimal scarring. During MIS procedures, a variety of instruments and surgical tools may be introduced into the abdominal cavity to engage and/or treat tissue in a number of ways to achieve a diagnostic or therapeutic effect. Various robotic systems have recently been developed to assist in MIS procedures by controlling such MIS instruments. A user (e.g., a surgeon) is able to remotely operate an MIS instrument's end effector by grasping and manipulating in space one or more controllers of the robotic system that communicate with a tool driver coupled to the surgical instrument. User inputs are processed by a computer system incorporated into the robotic surgical system and the tool driver responds by actuating the cable driven motion system and, more particularly, the drive cables. Moving the drive cables articulates the end effector to desired positions and configurations.

MIS instruments have limited life spans. For example, some MIS instruments are designed to expire after a predetermined number of uses or after a set period of time. In some cases, MIS instruments may include an indicator that provides indication when the useful life of the MIS instruments has been exhausted. Conventional instrument indicators are mechanically powered by one of the MIS instrument's tool drivers, which necessarily decreases overall functionality of the MIS instrument as such tool driver could instead be utilized for other tool functions. Moreover, conventional instrument indicators are not easily recognized and, consequently, sterilization workers often do not notice expired MIS instruments and are accidentally cleaned, sterilized, stored, and later sent to the operating room, despite having no useful operational life remaining. Once discovered in the operating room, personnel will be required to discard the MIS instrument and obtain a replacement. This results in frustration, procedural delay, and possible additional sedation time for the patient. Thus, it may be beneficial to provide indicators that do not utilize tool drivers and indicators that are more easily recognized.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function.

DETAILED DESCRIPTION

The present disclosure is related to robotic surgical systems and, more particularly, to tool life indicators for surgical tools.

Embodiments discussed herein describe a surgical tool that provides a visual indicator to a user, operator, or technician when the useful life of the surgical tool has been exhausted. The surgical tool can include a drive housing defining an indicator aperture, a drive input rotatably coupled to a bottom of the drive housing, and an indicator assembly arranged within the drive housing and actuatable to provide visual indication that the surgical tool has exhausted its useful life. The indicator assembly may include a coil spring operatively coupled to the drive input such that rotation of the drive input correspondingly torques the coil spring, and an indicator shaft extending from the indicator mount along a longitudinal axis coaxially aligned with the indicator aperture. The indicator shaft may be raised or lowered by the drive input to actuate the indicator assembly between a non-activated state, where the indicator shaft is recessed into the indicator aperture, and an activated state, where the indicator shaft extends out of the drive housing via the indicator aperture to provide the visual indication.

Figure 1:
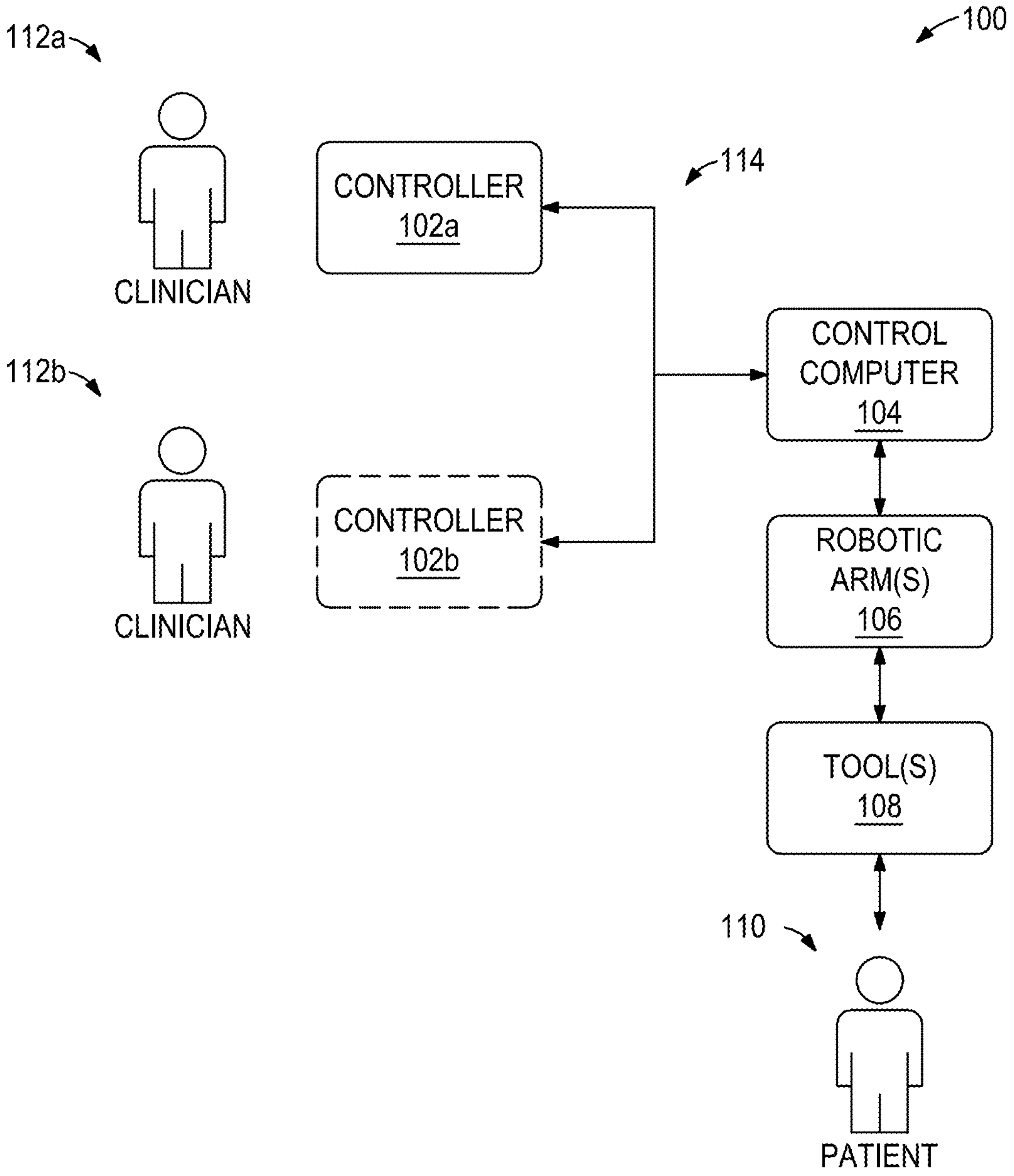
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between the clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
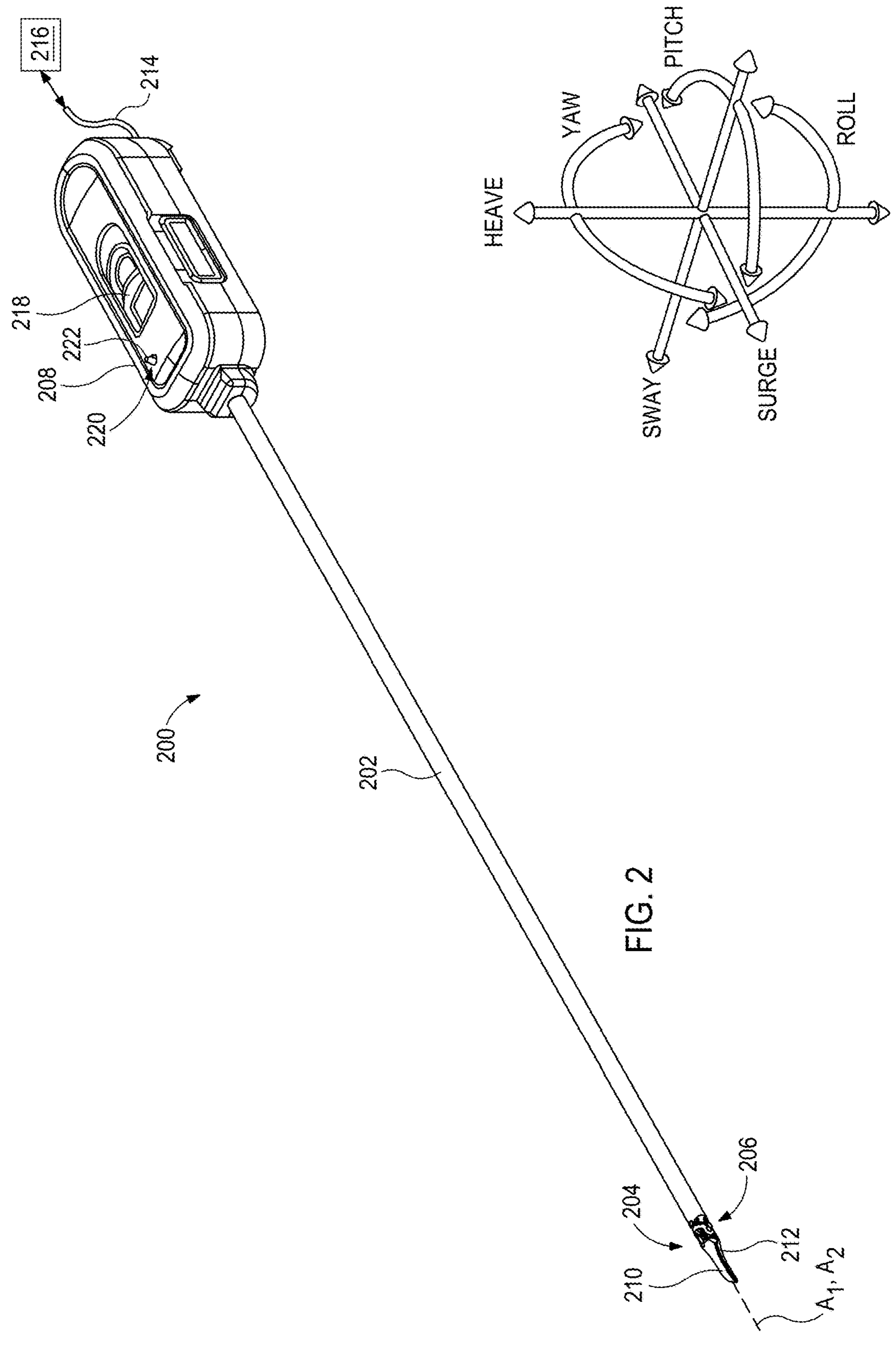
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can exhibit a variety of sizes, shapes, and configurations. In the illustrated embodiment, the end effector 204 comprises a combination tissue grasper and vessel sealer that include opposing first (upper) and second (lower) jaws 210, 212 configured to move (articulate) between open and closed positions. As will be appreciated, however, the opposing jaws 210, 212 may alternatively form part of other types of end effectors such as, but not limited to, a surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot to articulate the end effector 204 between the open and closed positions. In other embodiments, the end effector 204 may not include opposing jaws, but may instead comprise other types of surgical end effectors such as a stapler, a cauterizer, a suction tool, an irrigation tool, and the like.

FIG. 3 illustrates the potential degrees of freedom in which the wrist 206 may be able to articulate (pivot) and thereby move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Moving (actuating) one or more of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the housing 208. In other embodiments, the power cable 214 may be omitted and electrical power may be supplied to the surgical tool 200 via an internal power source, such as one or more batteries, capacitors, or fuel cells. In such embodiments, the surgical tool 200 may alternatively be characterized and otherwise referred to as an "electrosurgical instrument" capable of providing electrical energy to the end effector 204.

The power cable 214 may place the surgical tool 200 in electrical communication with a generator 216 that supplies energy, such as electrical energy (e.g., radio frequency energy), ultrasonic energy, microwave energy, heat energy, or any combination thereof, to the surgical tool 200 and, more particularly, to the end effector 204. Accordingly, the generator 216 may comprise a radio frequency (RF) source, an ultrasonic source, a direct current source, and/or any other suitable type of electrical energy source that may be activated independently or simultaneously.

In applications where the surgical tool 200 is configured for bipolar operation, the power cable 214 will include a supply conductor and a return conductor. Current can be supplied from the generator 216 to an active (or source) electrode located at the end effector 204 via the supply conductor, and current can flow back to the generator 216 via a return electrode located at the end effector 204 via the return conductor. In the case of a bipolar grasper with opposing jaws, for example, the jaws serve as the electrodes where the proximal end of the jaws are isolated from one another and the inner surface of the jaws (i.e., the area of the jaws that grasp tissue) apply the current in a controlled path through the tissue. In applications where the surgical tool 200 is configured for monopolar operation, the generator 216 transmits current through a supply conductor to an active electrode located at the end effector 204, and current is returned (dissipated) through a return electrode (e.g., a grounding pad) separately coupled to a patient's body.

The surgical tool 200 may further include a manual release switch 218 that may be manually actuated by a user (e.g., a surgeon) to override the cable driven system and thereby manually articulate or operate the end effector 204. The release switch 218 is movably positioned on the drive housing 208, and a user is able to manually move (slide) the release switch 218 from a disengaged position, as shown, to an engaged position. In the disengaged position, the surgical tool 200 is able to operate as normal. As the release switch 218 moves to the engaged position, however, various internal component parts of the drive housing 208 are simultaneously moved, thereby resulting in the jaws 210, 212 opening, which might prove beneficial for a variety of reasons. In some applications, for example, the release switch 218 may be moved in the event of an electrical disruption that renders the surgical tool 200 inoperable. In such applications, the user would be able to manually open the jaws 210, 212 and thereby release any grasped tissue and remove the surgical tool 200. In other applications, the release switch 218 may be actuated (enabled) to open the jaws 210, 212 in preparation for cleaning and/or sterilization of the surgical tool 200.

According to embodiments of the present disclosure, the surgical tool 200 may further include a tool end of life indicator assembly 220 that may be automatically activated (triggered) to provide a visual indication that the useful life of the surgical tool 200 has been exhausted and/or that the recommended lifespan of the surgical tool 200 has expired. The tool of life indicator assembly 220 may be alternately referred to herein as "the indicator assembly 220". Upon activation of the indicator assembly 220, the user will be visually notified that the service life of the surgical tool 200 has been exhausted and should not be cleaned for re-use but instead decommissioned (e.g., discarded).

In some examples, the surgical tool 200 may include a single tool end of life indicator assembly 220. In other examples, the surgical tool 200 may include a plurality of tool end of life indicator assemblies 220, where a first is activated after a first use, a second is activated after a second use, and so on; and activation of all of the plurality of tool end of life indicator assemblies 220 indicates that the surgical tool 200 has reached the end of its life. In at least one embodiment, the tool end of life indicator assembly 220 may provide a visual indication that the surgical tool 200 has a certain amount of life (or uses or hours of use) remaining.

Various metrics may be implemented to measure the useful life of the surgical tool 200. For example, the "useful life" may be determined by the number of procedures that the surgical tool 200 has been utilized (e.g., twenty procedures). In such embodiments, once the number of uses of the surgical tool 200 reaches a predetermined threshold, the indicator assembly 220 may be activated to visually inform the user. Alternatively, the "useful life" may be determined by the number of hours that the surgical tool 200 has been utilized, the number of articulations or movements that the surgical tool 200 has made, or any combination thereof. The indicator assembly 220 may provide a visually perceivable indication that the surgical tool 200 has exhausted its useful life or is expired, and/or that the surgical tool 200 has a certain amount of life (e.g., uses, hours of use, etc.) remaining.

As described in more detail below, the tool end of life indicator assembly 220 may include a mechanically actuated indicator button or shaft 222 that becomes visible (exposed) once the useful life of the surgical tool 200 has been exhausted or reached. In one or more embodiments, as illustrated, the indicator assembly 220 may be located on the drive housing 208, such as on a top surface of the drive housing 208. The indicator assembly 220, however, may be located at any location on the surgical tool 200 that sufficiently enables a user to visually notice the indicator shaft 222. During normal operation of the surgical tool 200, and before reaching the predetermined useful life threshold, the indicator shaft 222 may be recessed into the interior of the drive housing 208 and otherwise not visible. Once it is determined that the useful life of the surgical tool 200 has been exhausted, however, the indicator assembly 220 may be actuated (activated), which results in the indicator shaft 222 extending (protruding) a short distance out of the drive housing 208 to provide a visual indication to the user. The indicator assembly 220 is shown in FIG. 2 with the indicator shaft 222 in the activated state.

Figure 4:
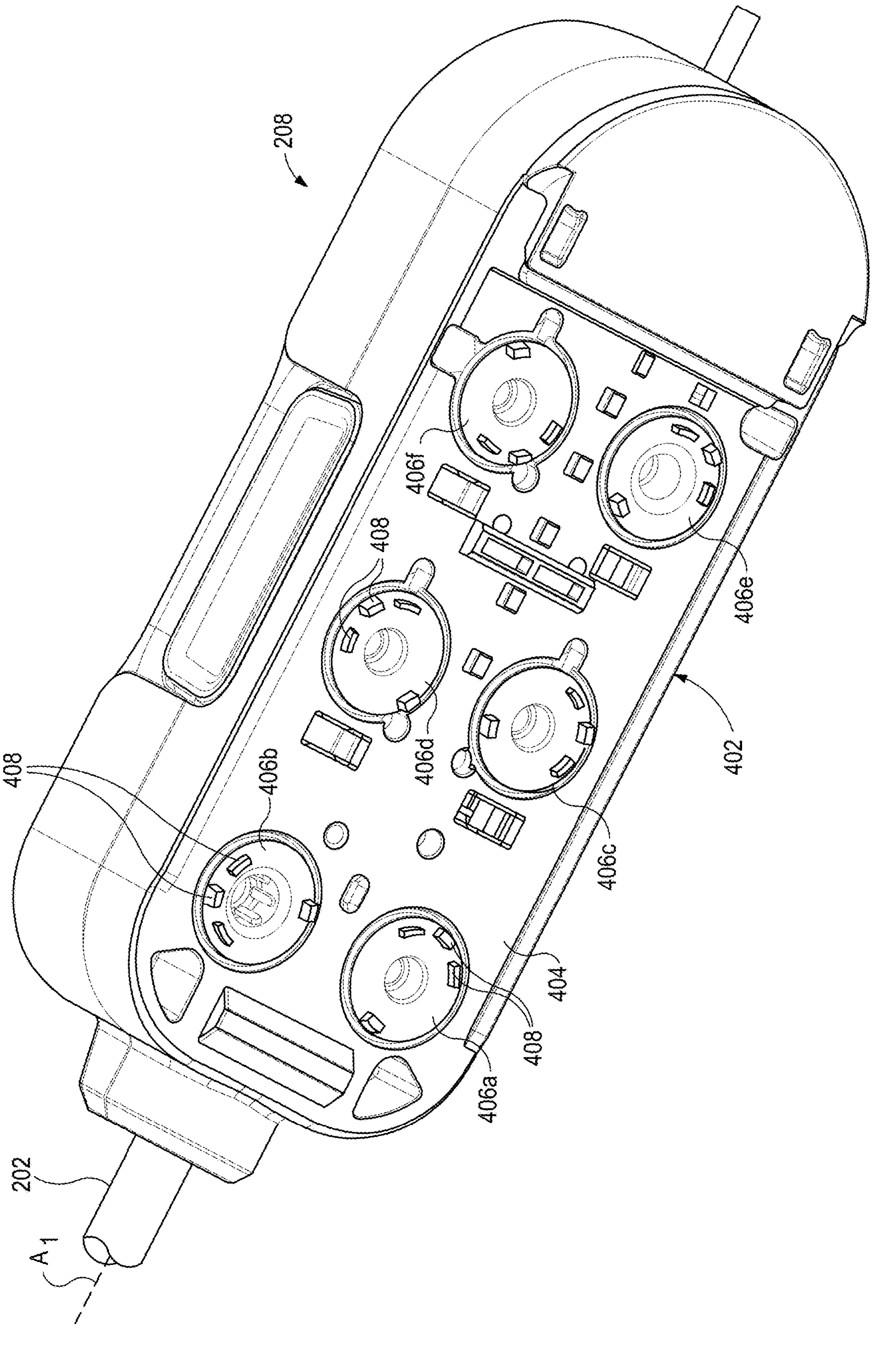
FIG. 4 is a bottom view of the drive housing of FIG. 2, according to one or more embodiments.

FIG. 4 is a bottom view of the drive housing 208, according to one or more embodiments. As illustrated, the drive housing 208 may include a tool mounting portion 402 used to operatively couple the drive housing 208 to a tool driver of a robotic manipulator. The tool mounting portion 402 may releasably couple the drive housing 208 to a tool driver in a variety of ways, such as by clamping thereto, clipping thereto, or slidably mating therewith. In some embodiments, the tool mounting portion 402 may include an array of electrical connecting pins, which may be coupled to an electrical connection on the mounting surface of the tool driver. While the tool mounting portion 402 is described herein with reference to mechanical, electrical, and magnetic coupling elements, it should be understood that a wide variety of telemetry modalities might be used, including infrared, inductive coupling, or the like.

The tool mounting portion 402 includes and otherwise provides an interface 404 configured to mechanically, magnetically, and/or electrically couple the drive housing 208 to the tool driver. As illustrated, the interface 404 includes and supports a plurality of drive inputs, shown as drive inputs 406*a*, 406*b*, 406*c*, 406*d*, 406*e*, and 406*f*. Each drive input 406*a-f* comprises a rotatable disc configured to align with and couple to a corresponding actuator or "drive output" of a tool driver, such that rotation (actuation) of a given drive output drives (rotates) a corresponding one of the drive inputs 406*a-f*. Each drive input 406*a-f* may provide or define one or more surface features 408 configured to align with mating surface features provided on the corresponding drive output. The surface features 408 can include, for example, various protrusions and/or indentations that facilitate a mating engagement. In some embodiments, some or all of the drive inputs 406*a-f* may include one surface feature 408 that is positioned closer to an axis of rotation of the associated drive input 406*a-f* than the other surface feature(s) 408. This may help to ensure positive angular alignment of each drive input 406*a-f*.

Actuation of the first drive input 406*a* may be configured to control actuation of the tool end of life indicator assembly 220 (FIG. 2). In some embodiments, actuating the first drive input 406*a* may not only control actuation of the indicator assembly 220, as described below, but may also control actuation of another feature or operation for the surgical tool 200 (FIG. 2). In other embodiments, however, actuating the first drive input 406*a* may solely control actuation of the indicator assembly 220, without departing from the scope of the disclosure.

Actuation of the second drive input 406*b* may be configured to control rotation of the shaft 202 about its longitudinal axis $A_1$. The shaft 202 may be rotated clockwise or counter-clockwise depending on the rotational actuation of the second drive input 406*b*. In some embodiments, actuation of the second, third, fourth, and fifth drive inputs 406*b-e* may be configured to operate movement (axial translation) of drive cables that form part of a cable driven motion system, which results in the actuation of the wrist 106 (FIG. 4) and/or articulation (operation) of the end effector 204 (FIG. 4). In some embodiments, actuation of the sixth drive input 406*f* may be configured to advance and retract a drive rod, and thereby correspondingly advance or retract a knife at the end effector 204. Each of the drive inputs 406*a-f* may be actuated based on user inputs communicated to the tool driver coupled to the interface 404, and the user inputs may be received via a computer system incorporated into the robotic surgical system.

The drive housing 208 may house electronics that store unique identification data for the surgical tool 200 (FIG. 2). Upon mounting the drive housing 208 to a tool driver of the robotic surgical system 100 (FIG. 1), the system 100 may be able to identify the type of tool and/or the specific tool utilized in a particular operation based on the unique identification data. In addition, the electronics of the surgical tool 200 may store the useful life of the surgical tool 200 (e.g., the use count), and the useful life of the surgical tool 200 may be determined by logic stored on one or more components of the robotic surgical system 100. Moreover, the surgical system 100 may store information related to a particular surgical tool 200, and then access and utilize that stored information when it recognizes that the particular surgical tool 200 is being utilized. For example, the robotic surgical system 100 may recognize that the surgical tool 200 has been installed in the robotic manipulator and then access its remaining useful life that was previously calculated, so that such useful tool life may be updated as needed following the particular operation in which the surgical tool 200 is being utilized.

The surgical tool 200 (FIG. 2) may wirelessly communicate with the robotic surgical system 100 (FIG. 1). In particular, the robotic surgical system 100 may utilize NFC protocols to identify or authenticate the surgical tool 200 or to associate the surgical tool 200 with stored data related to the surgical tool 200. In at least some embodiments, the surgical tool 200 includes a tag that may be read remotely and wirelessly, without physical contact, when excited with energy emitted from the robotic manipulator. The tag includes an integrated circuit (or chip) that stores and processes information and modulates and demodulates signals (i.e., radio frequency or "RF" signals) and an antenna that receives and transmits the signal. The tag may include a battery and periodically self-activate to transmit a signal, or may include a battery but activate to transmit a signal when in the presence of the robotic manipulator (or other reader device), or may not include a battery and activate to send a signal when excited by the robotic manipulator (or other reader device). The tag may be read-only, having information assigned thereon, or may be read/write, where information may be written into the tag one or more times.

In these examples, the robotic manipulator (or reader device) transmits an encoded radio signal to interrogate the tag within the surgical tool 200. The tag receives the encoded radio signal and responds by sending the identification and/or other information stored in the integrated circuit (e.g., serial number, use count, usage time, manufacture date, expiration date, etc.) to the robotic manipulator so that it may be analyzed by the robotic surgical system 100. Accordingly, the robotic surgical system 100 may be able to differentiate between a variety of surgical tools as the tags of each surgical tool will include unique identification data.

Figure 5A:
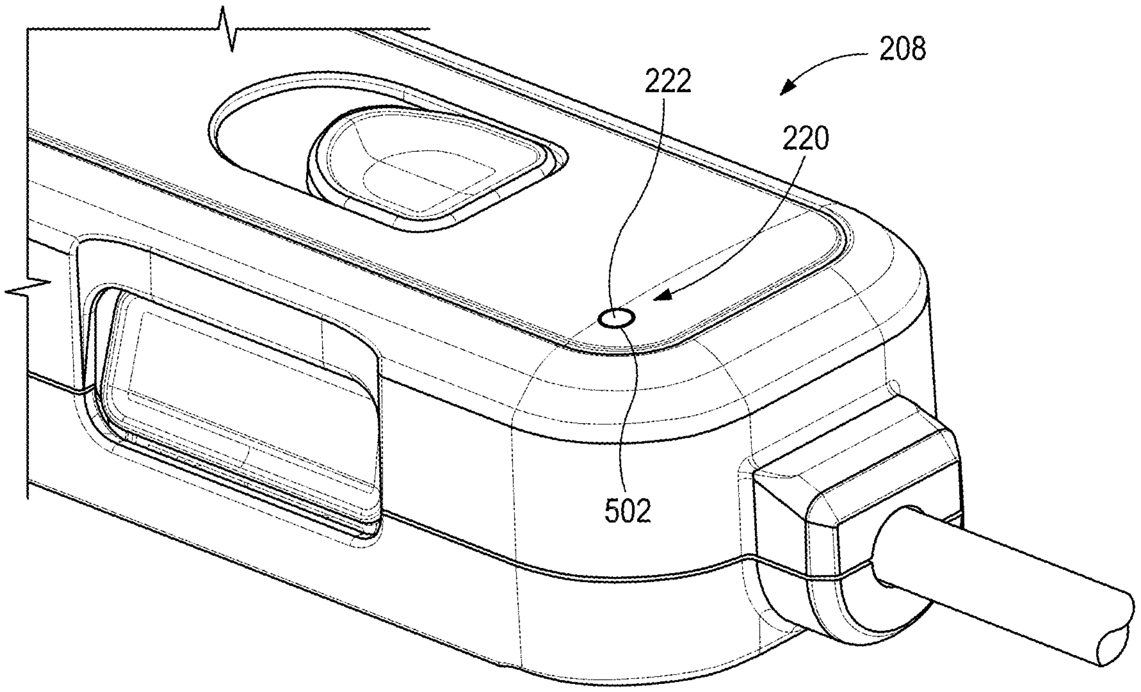
FIGS. 5A and 5B are isometric views of the drive housing of FIG. 2, according to one or more embodiments.
Figure 5B:
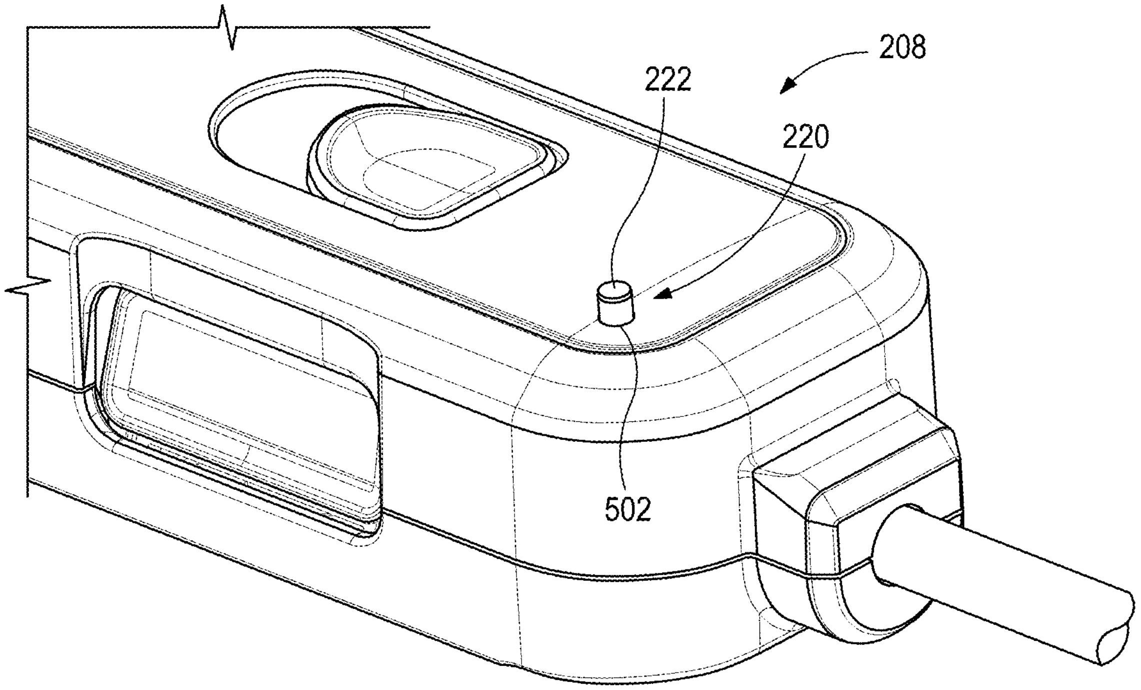

FIGS. 5A and 5B are isometric views of the drive housing 208, according to one or more embodiments. FIGS. 5A-5B also depict example actuation of the tool end of life indicator assembly 220, which includes the indicator shaft 222. In FIG. 5A, the indicator assembly 220 is in a first or "non-activated" state, and thus the indicator shaft 222 is not readily perceivable. However, in FIG. 5B, the indicator assembly 220 is transitioned to a second or "activated" state, and the indicator shaft 222 extends out of the drive housing 208 a short distance and is readily perceivable by an operator. The remaining portions of the indicator assembly 220 are housed within the drive housing 208, and various embodiments of the indicator assembly 220 will be discussed below.

When the indicator assembly 220 is in the non-activated state, as shown in FIG. 5A, the indicator shaft 222 is substantially or entirely received within the drive housing 208, such that the indicator shaft 222 is mostly or fully occluded from the view of an operator or user. In contrast, when the indicator assembly 220 is transitioned to the activated state, as shown in FIG. 5B, the indicator shaft 222 is moved such that the top or upper end of the indicator shaft 222 protrudes (extends) a short distance out of the drive housing 208 via an indicator aperture 502 defined in the drive housing 208. When the indicator shaft 222 protrudes out of the drive housing 208 via the indicator aperture 502, this provides a positive, visual indication that the surgical tool 200 (FIG. 2) has exhausted its useful life, and appropriate action should be taken.

Figure 6:
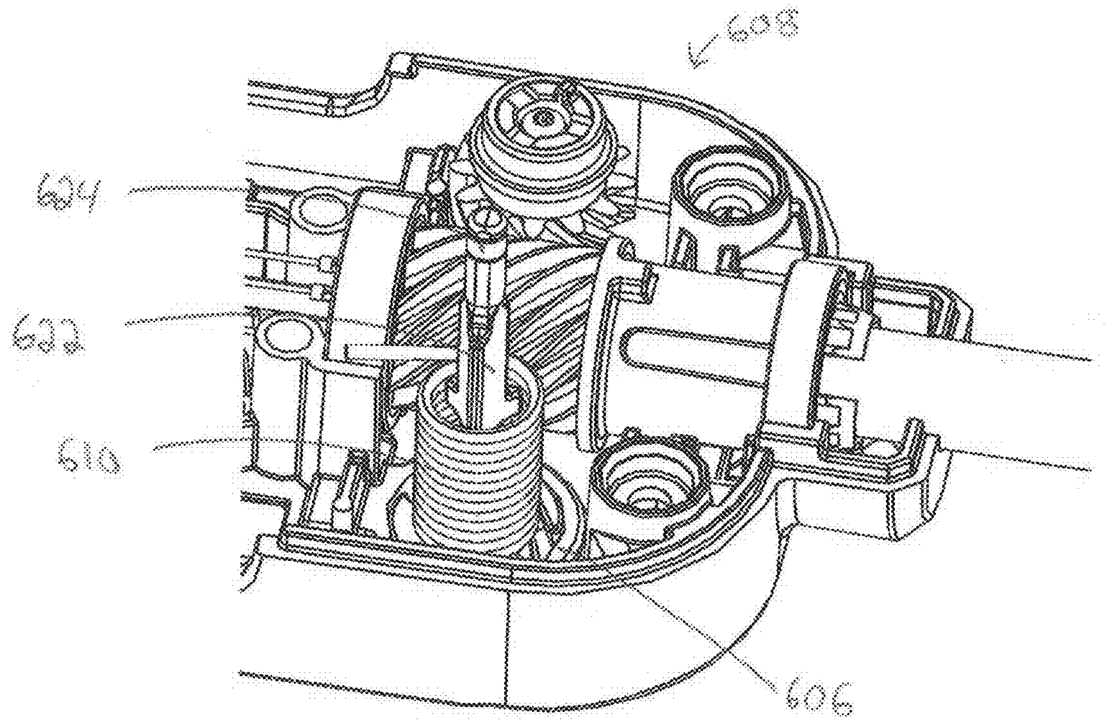
FIG. 6 is an exposed view of the interior of the drive housing, according to one or more embodiments.

FIG. 6 is an exposed view of indicator assembly 220 shown in FIGS. 5A & 5B. Indicator assembly 220 includes a drive input 606, a spring 610, indicator shaft 622 which further includes a visible upper section 624. Drive input 606 is retained in drive housing 608 and restricted from axial movement while permitted to rotate. A spring 610 is anchored between the drive housing 608 and drive input 606 as to apply a torsional load to drive input 606. The torsional load provided by spring 610 should be at least sufficiently high enough to prevent inadvertent rotation and activation of indicator assembly 220. It is desirable that the torsional load provided by spring 610 be sufficiently high enough that manual actuation from handling, cleaning, packaging, or transportation is prevented and only the tool driver is able to rotate drive input 606 thus activating indicator assembly 220.

Figure 7:
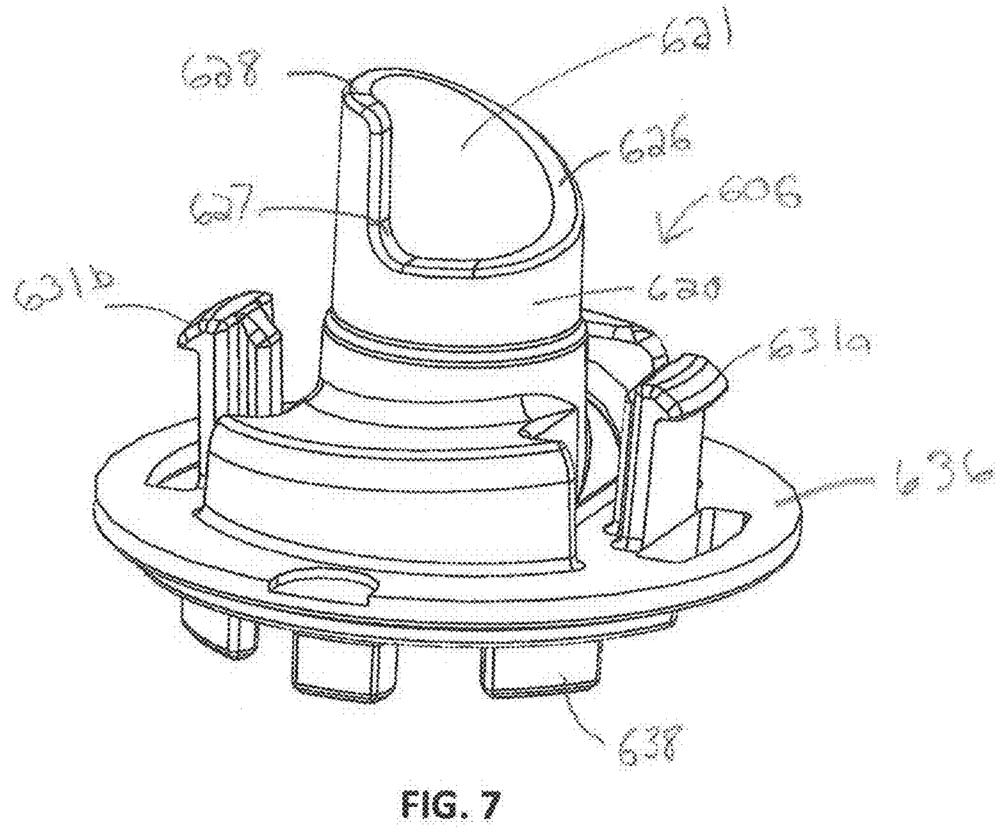
FIG. 7 is an isolated view of a drive input incorporate some or all of the principles of the present disclosure.
Figure 10A:
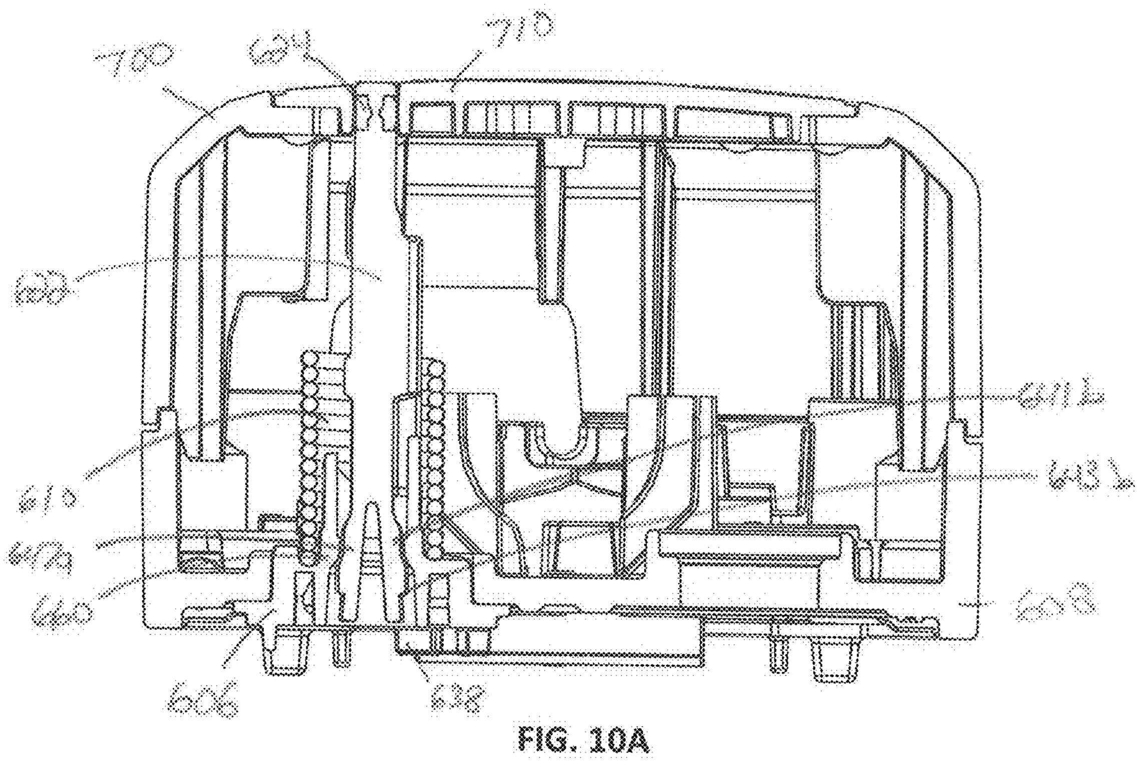
FIGS. 10A and 10B are sequential cross-sections of indicator assembly in a non-activated state and activated state, that may incorporate some or all of the principles of the present disclosure.
Figure 10B:
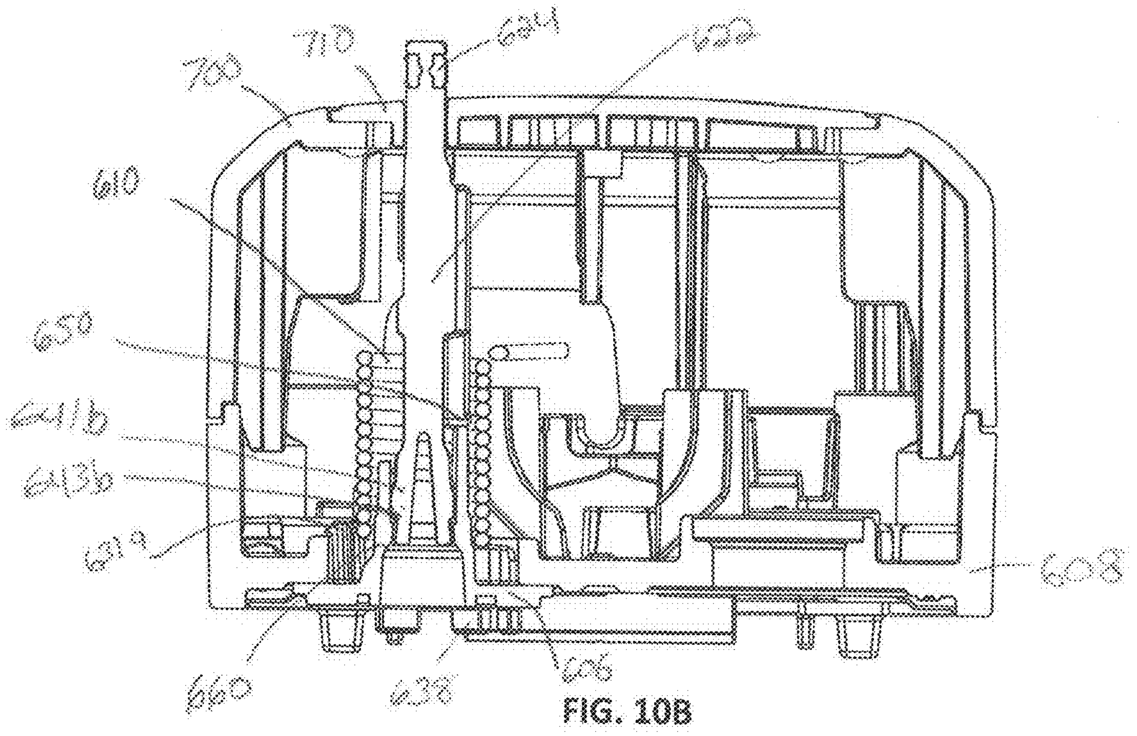

FIG. 7 is an isolated view of drive input 606 of indicator assembly 220. Drive input 606 is retained in housing 608 by hooks 631*a* and 631*b*. As seen in FIG. 10B, hooks 631*a* and 631*b* ride on the interior surface of housing 608 and prevent axial movement of drive input 606 in one direction while permitting rotation. As seen in FIG. 10A, face 636 of drive input 606 contacts the outer surface of drive housing 608 and prevents axial movement in the opposite direction as hooks 631*a* and 631*b* while still allowing rotation of drive input 606. Rotation of drive input 606 is achieved by coupling of surface features 638 with corresponding features on the tool drive. Surface features 638 transmit rotation from the tool drive to drive input 606. This rotation may be transmitted through a sterile barrier between surface features 638 and the corresponding features on the tool drive. Drive input 606 further contains a central riser 620. As shown in FIG. 10A, central riser 620 may contain an opening or passage 621 that houses indicator shaft 622. Passage 621 may vary in diameter as described in further detail below. Rim 626 of riser 620 may have a helical path that begins at a vertical face 627 and ends at a flat portion 628. Indicator shaft 622 rides along rim 626 and is driven longitudinally along its axis by rotation of drive input 606 about the same longitudinal axis, as is described below. The length, and pitch of the helical rim may be varied to tune the timing, distance, or input required to activate indicator assembly 220.

Figure 8A:
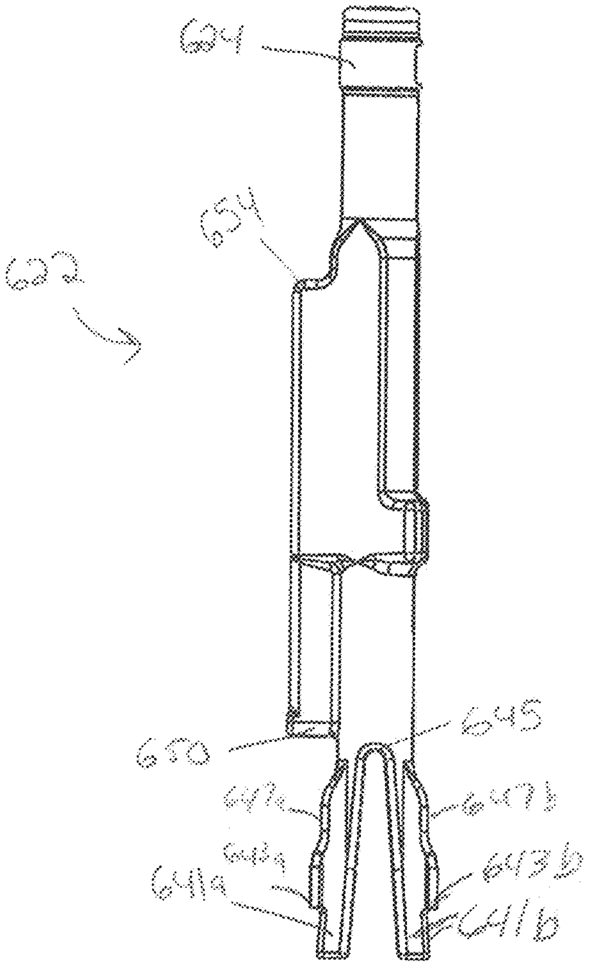
FIG. 8A is an isolated view of an indicator shaft, that may incorporate some or all of the principles of the present disclosure.
Figure 8B:
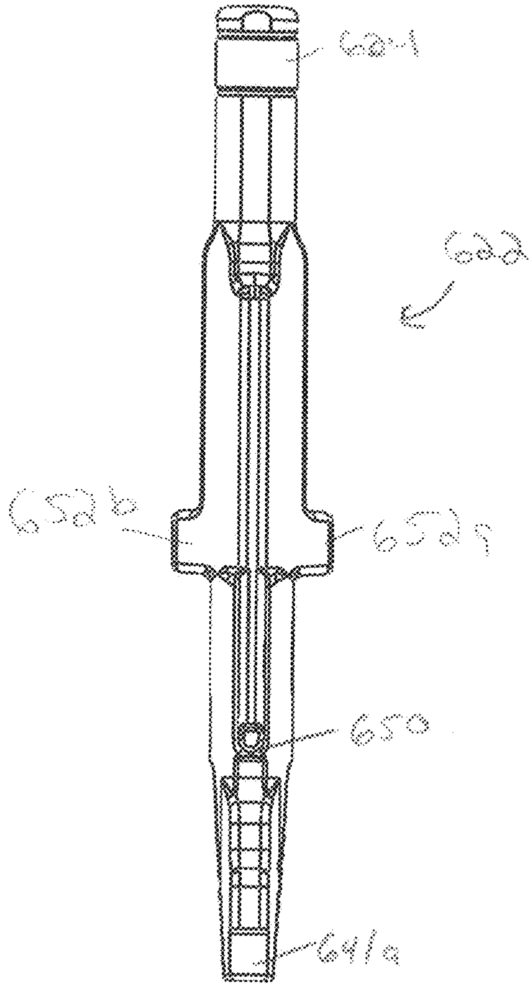
FIG. 8B is an isolated view of the indicator shaft of FIG. 8A rotated ninety degrees, that may incorporate some or all of the principles of the present disclosure.

FIGS. 8A and 8B show indicator shaft 622. Indicator shaft 622 has three main portions, a visible upper section, a middle actuation section, and a lower lockout section. The visible upper section 624 is either visible to the user in an activated state or not visible to the user in an inactivated state. Visible upper section 624 may include or exhibit a color (e.g., red), which may be easily perceivable by a user when transitioned to the activated state. Likewise, visible upper section 624 may include a light (e.g., a light-emitting diode or "LED") that is triggered to emit light (shine) when the indicator assembly 220 transitions to the activated state. The middle actuation section of indicator shaft 622 may contain a drive pin 650 which mates with rim 626 on drive input 606. As drive input 606 rotates drive pin 650 is driven by rim 626 and causes indicator shaft 622 to rise or fall along the helical path of rim 626. To keep the indicator shaft from rotating, the middle actuation section contains alignment fins. Distal fin 654 and medial fins 652*a*, and 652*b* prevent rotation of indicator shaft 622 while allowing axial movement along the longitudinal axis. Lastly, the lower lockout section of shaft 622 contains a bifurcation point 645 which produces two lower limbs 641*a* and 641*b*. While only two limbs are shown a plurality of 2 or more limbs are possible. Limbs 641*a* and 641*b* have a symmetrical profile about the longitudinal axis of indicator shaft 622. Both limbs 641*a* and 641*b* have a fin like profile starting at bifurcation point 645 and extending approximately three-quarters of the way down the limbs. Fins 647*a* and 647*b* have a curved or sloped geometry and protrude out from the longitudinal axis. The protrusion being greater the further from the bifurcation point 645. Fins 647*a* and 647*b* abruptly terminate and form a step at termination points 643*a* and 643*b*.

Figure 9C:
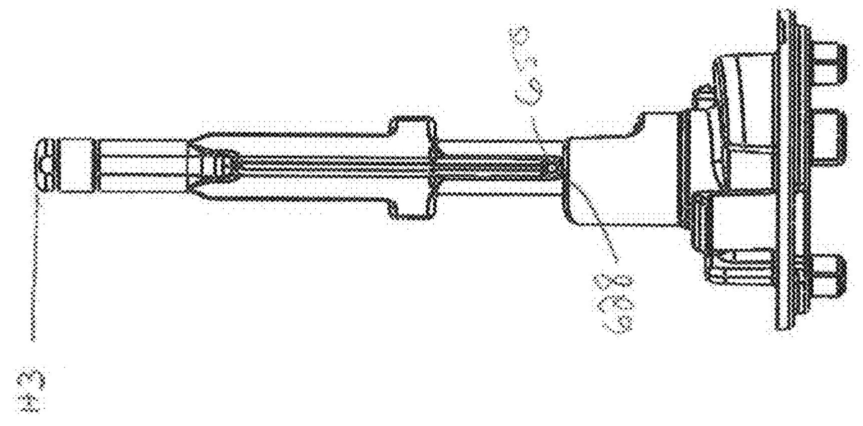
FIG. 9A-9C is a sequential view from a non-activated to activated state of the indicator assembly of FIG. 6.
Figure 9B:
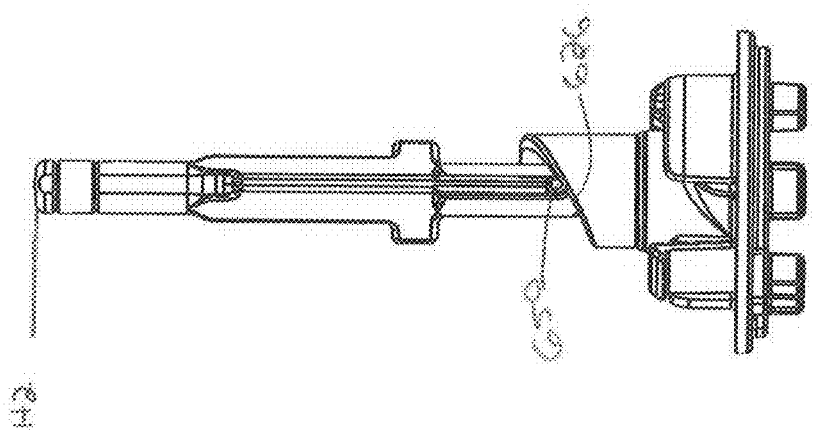
Figure 9A:
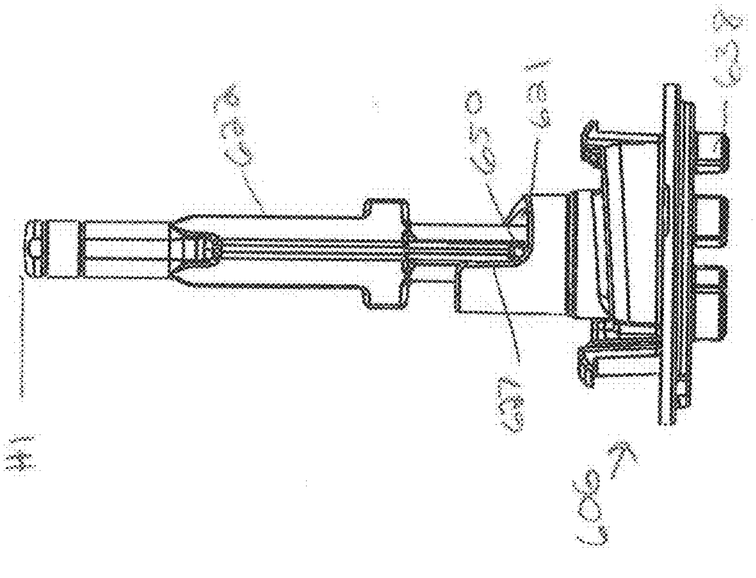

FIGS. 9A-9C illustrate the sequence of indicator shaft 622 being driven from an inactivated state to an activated state by drive input 606. As shown in the inactive state of FIG. 9A, indicator shaft 622 has an initial height H1 and resides inside passage 621 of riser 620. Drive pin 650 of indicator shaft 622 rest on rim 626 against the vertical face 627. FIG. 9B shows a middle activation state where indicator assembly is between inactive and a fully activated state. Drive input 606 is coupled to the tool drive which transfers rotary motion to drive input via surface features 638. As drive input 606 rotates, the drive pin 650 follows the helical path of rim 626 and begins to raise the indicator shaft from an initial height H1 to an intermediate height H2 that is higher than H1. FIG. 9C shows indicator assembly in a fully activated state. Drive pin 650 has traveled across the entire helical path of rim 626 and is now on the flat portion 628 of rim 626 which has risen indicator shaft 622 to a final, fully activated, height of H3 which is greater than H2.

FIG. 10A shows the cross-section view of indicator assembly 222 within drive housing 608. Drive housing 608 contains and upper housing 700 and a top cover 710. While in the inactive state, visible upper section 624 of indicator shaft 622 is retained within top cover 710 and upper housing 700 and not visible to the user. Passage 621 on drive input 606 has an hourglass like profile with a defined neck portion 660 between a smaller diameter portion and larger diameter portion with the larger diameter portion being closer to surface features 638 and the tool drive. In the initial position, neck portion 660 contacts limbs 641*a* and 641*b* at fins 647*a* and 647*b* and termination points 643*a* and 643*b* are within the larger diameter portion of passage 621. As the indicator assembly 222 is activated and indicator shaft begins to rise from H1 to H3 the fins 647*a* and 647*b* begin to ride along neck portion 660 which compresses limbs 641*a* and 641*b* towards each other. As can be seen in FIG. 10B, once the termination points 643*a* and 643*b* pass neck portion 660 and are now within the smaller diameter portion of passage 621 limbs 641*a* and 641*b* are released and expand outward. The indicator shaft 622, at this point, is fully activated and visible upper section 624 is clear of upper housing 700 and top cover 710 and is now visible to the user. Furthermore, in the fully activated state, indicator shaft 222 is unable to move proximally back into housing 608 because termination points 643*a* and 643*b* are flush with the steps formed by neck portion 660 within the smaller diameter portion of passage 621. This serves as a lockout feature so that once deployed in an activated state, indicator assembly 222 is prevent from being advanced back into the drive housing 608 without disassembling the entire drive housing 608.

Figure 11:
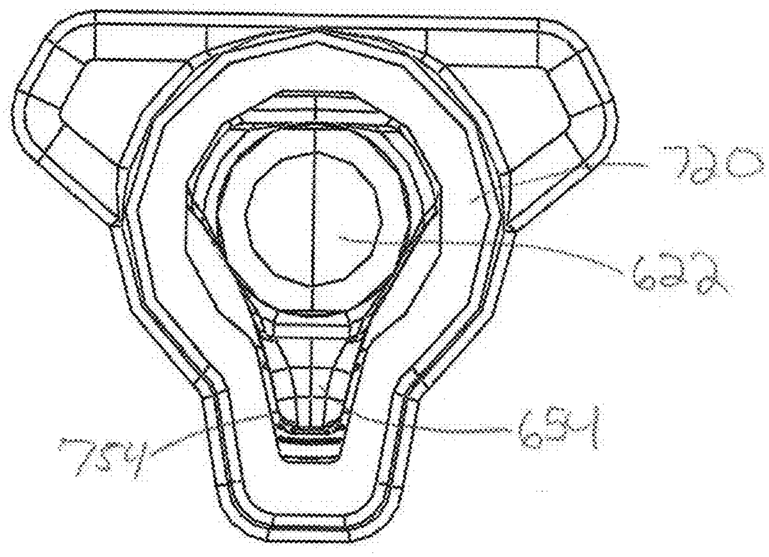
FIG. 11 is an isolated top-down view of indicator shaft aligned within a drive housing, that may incorporate some or all of the principles of the present disclosure.
Figure 12:
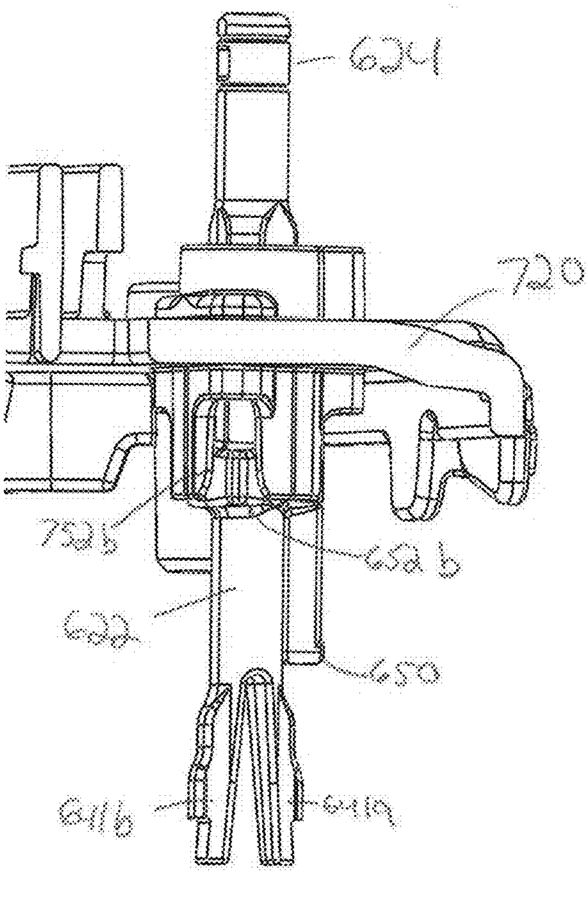
FIG. 12 is a cross section of an indicator assembly, that may incorporate some or all of the principles of the present disclosure.
Figure 13:
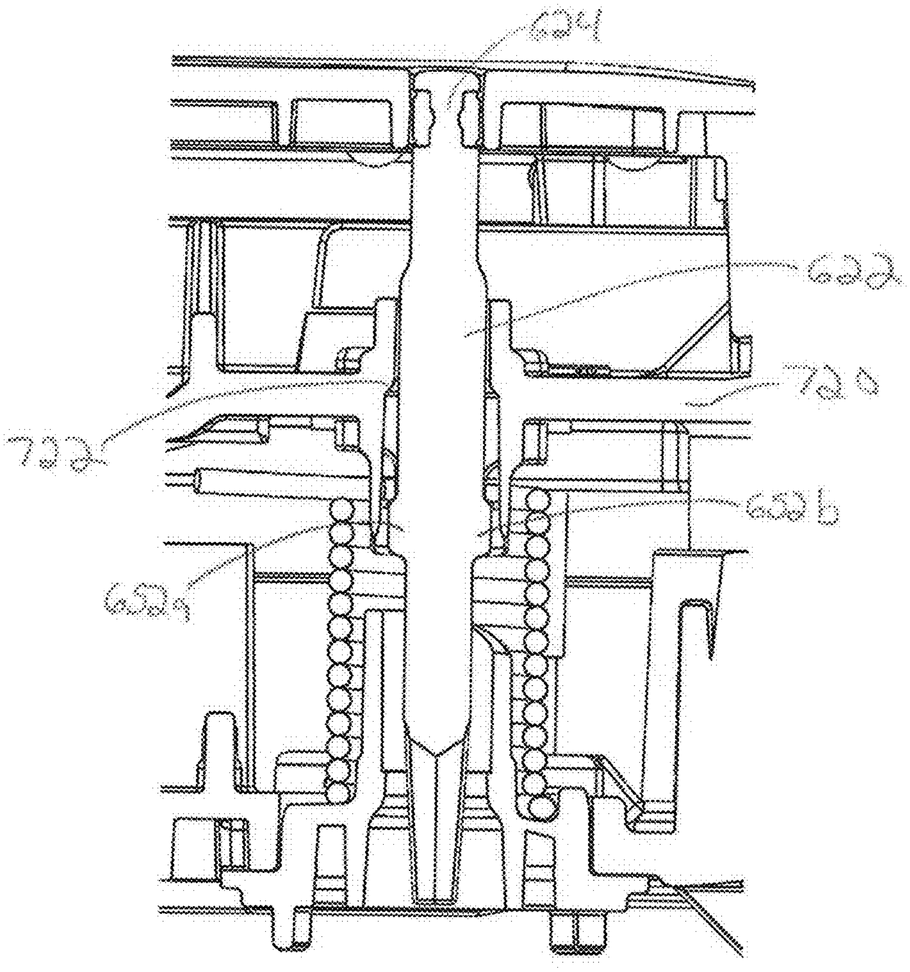
FIG. 13 is an isolated view of indicator shaft aligned within a drive housing, that may incorporate some or all of the principles of the present disclosure.

FIG. 11 is a top-down view of an alignment feature that may be utilized to keep indicator shaft 622 from rotating about its longitudinal axis. As drive input 606 rotates and guide pin 650 begins to travel about the helical path of rim 626, the indicator shaft 622 should be isolated and restrained from this rotation about the longitudinal axis yet free to travel longitudinally. Accordingly, as shown in FIG. 13, alignment plate 720 has a through hole that is coaxial with indicator shaft 622 which permits axially movement of indicator shaft 622 relative to alignment plate 720. To facilitate axial alignment and rotational restrain, indicator shaft 622 may include one or more alignment fins (654, 652*a*, and 652*b* shown in FIGS. 8A & 8B) that mate with one or more matching recesses 754, 752*a* (hidden), and 752*b* in alignment plate 720. When drive input 606 actuates the indicator shaft 622 distal fin 654 travels vertically within recess 754 along the longitudinal axis and is restrained from rotation by recess 754. Likewise, as can be seen in FIG. 12, medial fin 652*b* travels vertically within recess 752*b* but is restrained from rotation by recess 752*b*. While only medial fin 652*b* is shown, medial fin 652*a* (shown in FIG. 8B) also travels within corresponding recess 752*a* in alignment plate 720. Further, while only three alignment features are shown, alternate embodiments may use more or less than three alignment features.

FIG. 13 shows an anti-tamper feature of one or more embodiments. As previously described above, when the indicator assembly 220 is in an inactive state, the indicator shaft 622 is recessed within upper housing 700 and top cover 710. However, once indicator assembly 220 is in an activated state, the visible upper section 624 of indicator shaft 622 protrudes above upper housing 700 and top cover 710 and is thus exposed. Also, as described above, indicator shaft 622 is restrained from rotation but is free to move vertically along its longitudinal axis. Too much travel along the longitudinal axis in a direction protruding out from upper housing 700 and top cover 710 may damage the indicator assembly or surgical tool. It is therefore desirable to prevent excessive extraction of indicator shaft 622 vertically out of upper housing 700 and top cover 710. To prevent this excessive vertical movement, the through hole of alignment plate 720 has a narrowing 722. Medial fins 652*a* and 652*b* on indicator shaft 622 have a larger diameter about the longitudinal axis than the rest of indicator shaft 622. As the indicator shaft 622 travels distally along the longitudinal axis, so does the larger diameter portion of indicator shaft 622 that contains medial fins 652*a* and 652*b*. At a set maximum protrusion height of indicator shaft 622, medial fins 652*a* and 652*b* will encounter narrowing 722. Since the diameter of indicator shaft 622 about medial fins 652*a* and 652*b* is larger than that of narrowing 722, indicator shaft 622 is prevented from any further axial movement in the distal direction.

Embodiments disclosed herein include:

A. A surgical tool including a drive housing, an indicator assembly arranged within the drive housing and actuatable to provide visual indication that the surgical tool has exhausted its useful life. The indicator assembly includes a drive input rotatably coupled to the bottom of the drive housing. The drive input further including a riser and a rim where the riser contains a passage therethrough. The indicator assembly further includes an indicator shaft extending through the passage along a longitudinal axis coaxially aligned with the drive input. The drive input is rotated to actuate the indicator assembly between a non-activated state, where the indicator shaft is recessed into the drive housing, and an activated state, where the indicator shaft extends out of the drive housing to provide the visual indication.

B. A method of operating a surgical tool that includes determining that a useful life of the surgical tool has been exhausted. The surgical tool includes a drive housing and an indicator assembly arranged within the drive housing. The indicator assembly includes a drive input rotatably coupled to a bottom of the drive housing and an indicator shaft extending through the drive input along a longitudinal axis, and a coil spring anchored between the housing and the drive input. Rotating the drive input actuates the indicator assembly between a non-activated state, where the indicator shaft is recessed into the drive housing, and an activated state, where the indicator shaft extends out of the drive housing. The activation of the indicator assembly providing a visual indication with the indicator shaft that the useful life of the surgical tool has been exhausted.

Each of embodiments A and B may have one or more of the following additional elements in any combination: Element 1: wherein the rim forms a helical path. Element 2: wherein the indicator shaft includes a guide pin that follows the helical path so that rotation of the drive input actuates the indicator shaft along the longitudinal axis. Element 3: wherein the rim further includes a flat face and a vertical face on opposing sides of said helical path. Element 4: wherein the guide pin is adjacent to the vertical face when indicator assembly is in a non-activated state and resting on the flat face when said indicator assembly is in an activated state. Element 5: wherein the indicator assembly further includes a coil spring extending about the indicator shaft and operable to build spring force as guide pin progressively and sequentially engages the helical path. Element 6: wherein a bottom of the coil spring engages the drive input, and a top of the coil spring engages a static portion of the drive housing. Element 7: wherein said indicator shaft includes a visible upper section, said visible upper section is concealed within the drive housing and not visible in a non-activated state and extended beyond the drive housing and visible in an activated state. Element 8: wherein the visible upper section is distinctly colored, wherein the color is indicative of an end-of-life status of the tool. Element 9: wherein the visible upper section is illuminated. Element 10: wherein the passage contains a neck portion that separates a smaller diameter portion and a larger diameter portion. Element 11: wherein the indicator shaft includes at least two limb bodies, wherein the limb bodies are contained in the larger diameter portion of the passage in a non-activated state of said indicator assembly and contained within the smaller diameter portion of the passage when said indicator assembly is in an activated state. Element 12: wherein the limb bodies are compressed towards each other by the neck portion of said passage while transitioning from said non-activated state to said activated state. Element 13: wherein the limbs of said indicator shaft, once within the smaller diameter portion of said passage are prevented from moving back to the larger diameter portion said passage.

By way of non-limiting example, exemplary combinations applicable to A and B include: Element 1 with Element 2; Element 2 with Element 3; Element 3 with Element 4; Element 4 with Element 5; Element 5 with Element 6; Element 6 with Element 7; Element 7 with Element 8; Element 8 with Element 9; Element 10 with Element 11; Element 11 with Element 12; Element 12 with Element 13; Element 14 with Element 15; Element 15 with Element 16; Element 17 with Element 18; Element 17 with Element 19; Element 15 with Element 19; Element 19 with Element 20; and Element 21 with Element 22.

What is claimed is:

1. A surgical tool, comprising:

a drive housing; and an indicator assembly arranged within the drive housing and actuatable to provide visual indication that the surgical tool has exhausted its useful life, the indicator assembly including:

a drive input rotatably coupled to a bottom of the drive housing with a riser and a rim where said riser contains a passage therethrough; and an indicator shaft extending through said passage along a longitudinal axis coaxially aligned with the drive input, wherein the drive input is rotated to actuate the indicator assembly between a non-activated state, where the indicator shaft is recessed into the drive housing, and an activated state, where the indicator shaft extends out of the drive housing to provide the visual indication.

2. The surgical tool of claim 1, wherein the rim forms a helical path.

3. The surgical tool of claim 2, wherein the indicator shaft includes a guide pin that follows the helical path so that rotation of the drive input actuates the indicator shaft along the longitudinal axis.

4. The surgical tool of claim 3, wherein the rim further includes a flat face and a vertical face on opposing sides of said helical path.

5. The surgical tool of claim 4, wherein the guide pin is adjacent to the vertical face when indicator assembly is in a non-activated state and resting on the flat face when said indicator assembly is in an activated state.

6. The surgical tool of claim 5, wherein the indicator assembly further includes:

a coil spring extending about the indicator shaft and operable to build spring force as guide pin progressively and sequentially engages the helical path.

7. The surgical tool of claim 6, wherein a bottom of the coil spring engages the drive input, and a top of the coil spring engages a static portion of the drive housing.

8. The surgical tool of claim 7, wherein said indicator shaft includes a visible upper section, said visible upper section is concealed within the drive housing and not visible in a non-activated state and extended beyond the drive housing and visible in an activated state.

9. The surgical tool of claim 8, wherein the visible upper section is distinctly colored, wherein the color is indicative of an end-of-life status of the tool.

10. The surgical tool of claim 9, wherein the visible upper section is illuminated.

11. The surgical tool of claim 1, wherein the passage contains a neck portion that separates a smaller diameter portion and a larger diameter portion.

12. The surgical tool of claim 11, wherein the indicator shaft includes at least two limb bodies, wherein the limb bodies are contained in the larger diameter portion of the passage in a non-activated state of said indicator assembly and contained within the smaller diameter portion of the passage when said indicator assembly is in an activated state.

13. The surgical tool of claim 12, wherein the limb bodies are compressed towards each other by the neck portion of said passage while transitioning from said non-activated state to said activated state.

14. The surgical tool of claim 13, wherein the limbs of said indicator shaft, once within the smaller diameter portion of said passage are prevented from moving back to the larger diameter portion said passage.

15. A method of operating a surgical tool, comprising:

determining that a useful life of the surgical tool has been exhausted, the surgical tool including a drive housing, and an indicator assembly arranged within the drive housing, the indicator assembly including:

a drive input rotatably coupled to a bottom of the drive housing with a riser and a rim, where said riser contains a passage therethrough; and an indicator shaft extending through the drive input along a longitudinal axis; and a coil spring anchored between the housing and the drive input;

rotating the drive input and thereby actuating the indicator assembly between a non-activated state, where the indicator shaft is recessed into the drive housing, and an activated state, where the indicator shaft extends out of the drive housing; and providing a visual indication with the indicator shaft that the useful life of the surgical tool has been exhausted.

16. The surgical tool of claim 15, wherein the rim forms a helical path.

17. The surgical tool of claim 16, wherein the indicator shaft includes a guide pin that follows the helical path so that rotation of the drive input actuates the indicator shaft along the longitudinal axis.

18. The surgical tool of claim 17, wherein the rim further includes a flat face and a vertical face on opposing sides of said helical path.

19. The surgical tool of claim 18, wherein the guide pin is adjacent to the vertical face when indicator assembly is in a non-activated state and resting on the flat face when said indicator assembly is in an activated state.

20. The surgical tool of claim 15, wherein the passage contains a neck portion that separates a smaller diameter portion and a larger diameter portion.

21. The surgical tool of claim 20, wherein the indicator shaft includes at least two limb bodies, wherein the limb bodies are contained in the larger diameter portion of the passage in a non-activated state of said indicator assembly and contained within the smaller diameter portion of the passage when said indicator assembly is in an activated state.

22. The surgical tool of claim 21, wherein the limb bodies are compressed towards each other by the neck portion of said passage while transitioning from said non-activated state to said activated state.

23. The surgical tool of claim 22, wherein the limbs of said indicator shaft, once within the smaller diameter portion of said passage are prevented from moving back to the larger diameter portion said passage.

* * * * *